United States Patent [19]
Adams et al.

[11] Patent Number: 5,683,403
[45] Date of Patent: Nov. 4, 1997

[54] IMPLANTABLE LEAD SUTURE SLEEVE

[75] Inventors: John M. Adams, Issaquah; Clifton A. Alferness, Redmond, both of Wash.

[73] Assignee: InControl, Inc., Redmond, Wash.

[21] Appl. No.: 630,920

[22] Filed: Apr. 5, 1996

[51] Int. Cl.$^6$ ........................................ A61B 17/08
[52] U.S. Cl. .................. 606/151; 604/174; 607/149; 128/639; 128/644
[58] Field of Search ........................... 606/151, 157, 606/152; 604/174, 178, 179; 607/149, 130, 152; 128/639, 644; 24/17 A, 17 AP, 270, 19

[56] References Cited

U.S. PATENT DOCUMENTS

| | | | |
|---|---|---|---|
| 4,317,262 | 3/1982 | Wells, Jr. | 24/16 PB |
| 4,570,303 | 2/1986 | Richmond et al. | 24/16 PB |
| 4,971,272 | 11/1990 | Gudridge et al. | 248/74.5 |
| 5,267,967 | 12/1993 | Schneider | 604/174 |
| 5,423,763 | 6/1995 | Helland et al. | 604/174 |
| 5,549,619 | 8/1996 | Peters et al. | 606/151 |

*Primary Examiner*—Michael Buiz
*Assistant Examiner*—Tina T. D. Pham
*Attorney, Agent, or Firm*—Richard O. Gray, Jr.

[57] ABSTRACT

A suture sleeve fixes an implanted cardiac device lead to body tissue beneath the skin of a patient. The suture sleeve includes a base, and suture holes permitting the suture sleeve to be suture to the body tissue. A flexible strap member extends from the base for encircling the lead and includes at least one ratchet tooth. A pawl within the base lockingly engages the flexible strap ratchet tooth after the strap is wrapped about the lead.

11 Claims, 2 Drawing Sheets

IMPLANTABLE LEAD SUTURE SLEEVE

BACKGROUND OF THE INVENTION

The present invention generally relates to suture sleeves for fixating implanted leads, associated with implantable cardiac devices, to body tissue beneath the skin of a patient.

Suture sleeves find use for fixing an implanted lead beneath the skin of a patient. Prior art suture sleeves generally include a cylindrical member carrying one or more suture tie-downs and a circumferential suture receiving outer groove. The suture receiving groove receives suture and permits the suture sleeve to be wrapped and tied for securing the suture sleeve to the lead. Such sleeves are generally formed of flexible material, such as silicone.

In use, the lead to be implanted is first fed through the suture sleeve. Once the lead is in its implanted position, the suture sleeve is wrapped with suture in the suture receiving groove. The suture is pulled tight and tied to longitudinally fix the suture sleeve on the lead. The suture sleeve is then sutured to body tissue by using one or more suture tie-downs on the suture sleeve. If all goes well, the lead is fixed within the body of the patient.

Unfortunately, all does not always go well. For example, sometimes the suture about the suture sleeve is not pulled tight enough. This leaves the suture sleeve too loose on the lead and permits the lead to slide, and thus move, in a longitudinal direction. In such use, dislodgment of the leads or at least improper lead positioning is a distinct possibility.

Further, sometimes the suture about the suture sleeve is pulled too tight. This can result in the suture cutting through both the suture sleeve and the insulation about the lead. When this happens, the lead is damaged and must be replaced. Unfortunately, the damage is not usually detected until months or years later, requiring an additional and separate surgery to correct the problem.

The present invention provides suture sleeves which solve these problems. The present invention assures that the lead body of an implanted lead will be circumferentially held by the suture sleeve with an appropriate force which is neither too tight nor too loose. Further, the present invention avoids the need for suture being circumferentially wrapped about the suture sleeve and the lead body of the lead to be fixated. Hence, the lead is protected from destruction in the implant procedure and it is assured that the lead will be longitudinally held in place.

SUMMARY OF THE INVENTION

The presentation invention provides a suture sleeve for gripping the body of an implanted lead associated with an implanted cardiac device for fixation of the lead with respect to body tissue. The suture sleeve includes a base, securing means for securing the suture sleeve to the body tissue, a flexible strap extending from the base, and receiving means carried by the base for receiving the flexible strap. The strap defines a confining perimeter when encircling the lead body and received by the receiving means. The suture sleeve further includes locking means for locking the flexible strap with respect to the receiving means, and limit means for limiting a locked confining perimeter defined by the flexible strap to a predetermined minimum dimension.

The invention further provides a suture sleeve for fixating an implanted cardiac device lead to body tissue. The suture sleeve includes a base, at least one suture hole permitting the suture sleeve to be sutured to body tissue, a flexible strap member extending from the base and including at least one ratchet tooth, and pawl means within the base for lockingly receiving the flexible strap member.

In accordance with other aspects of the present invention, the flexible strap member defines a lead receiving circumference when received by the pawl means and the at least one ratchet tooth defines a minimum locked circumference of the flexible strap member.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein:

DETAILED DESCRIPTION OF THE PREFERRED EMBODIMENT

Figure 1:
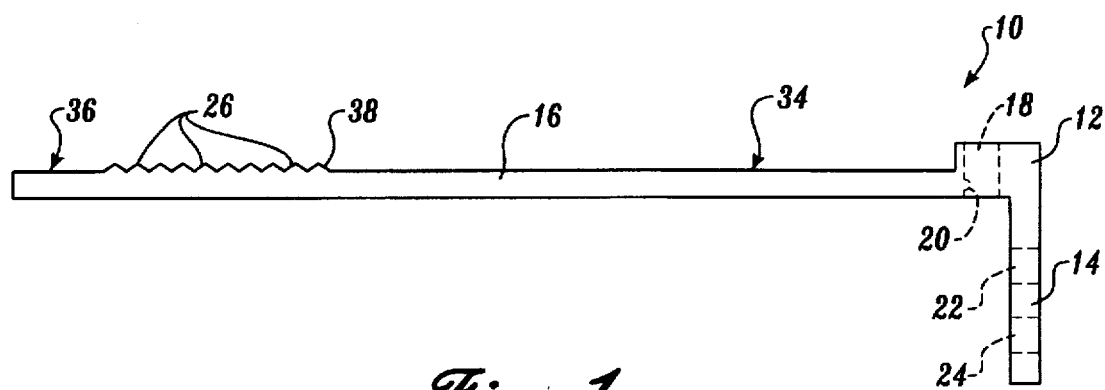
FIG. 1 is a side plan view of a suture sleeve embodying the present invention.
Figure 2:
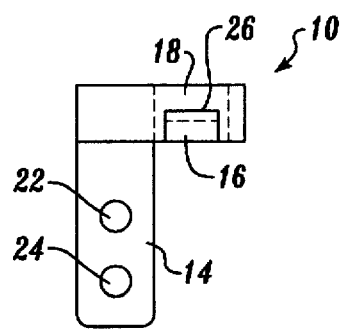
FIG. 2 is a end plan view of the suture sleeve of FIG. 1.

Referring now to FIGS. 1 and 2, a suture sleeve 10 embodying the present invention includes a base 12, a suture wing 14, a flexible strap 16 extending from the base 12, a channel 18 for receiving the strap, and a locking arrangement including a pawl 20. The suture wing 14 includes a pair of suture holes 22 and 24 to permit the suture sleeve 10 to be secured to body tissue beneath the skin of a patient.

The strap 16 includes a plurality of ratchet teeth 26. The ratchet teeth 26 are configured to engage the pawl 20 when the suture sleeve is in use for locking the strap 16 to the base 12 and circumferentially about the lead body of a lead to be fixated.

Figure 3:
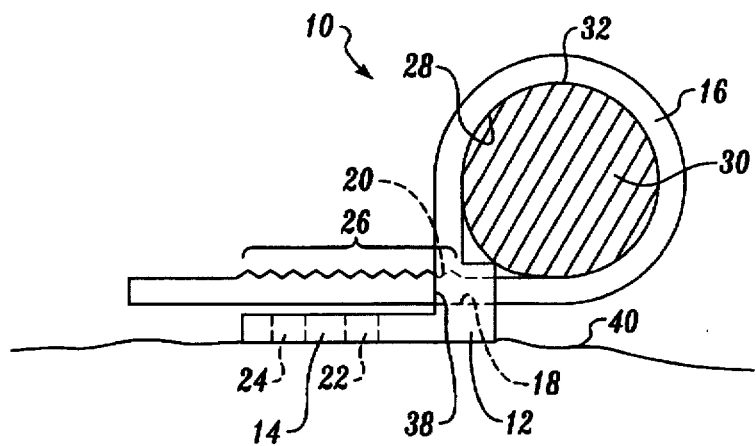
FIG. 3 is a side plan view illustrating the use of the suture sleeve of FIGS. 1 and 2.

The suture sleeve 10 is preferably formed of a flexible plastic material, such as polyurethane, polythylene, polysulfone, polypropylene, teflon, or other biodurable/biocompatable polymer. FIG. 3 illustrates the suture sleeve 10 in use for fixating a lead shown in cross-hatch at 30.

In FIG. 3 it can be seen that the flexible strap 16 has been encircled about the lead body 32 of lead 30 to define a confining perimeter 28 and is received by the channel 18 of the base 12. The flexible strap 16 as may be best seen in FIG. 1 has a proximal end 34 and a distal end 36 with respect to the base 12. The most proximal tooth 38 of the ratchet teeth 26 is preferably spaced from the base 12, and more particularly the pawl 20, by a distance which is slightly less than the non-deformed circumference of the lead body 32. Hence, the confirming perimeter 28 is slightly less in linear dimension than the circumference of the lead body 32.

There are no other ratchet teeth proximal from ratchet tooth 38. Hence, ratchet tooth 38 will serve to limit the locked confining perimeter defined by the flexible strap to a predetermined dimension which, as previously mentioned, is slightly less than the circumference of the lead body 32. The result is that the suture sleeve will be neither too loose nor too tight on the lead 30. Because the locked minimum confining perimeter dimension is fixed, the suture sleeve 10 will be precluded from either being too loose on the lead 30 or too tight on the lead 30 to eliminate the possibility of damaging the lead.

Of course, the suture holes 22 and 24 may be used to secure the suture sleeve to body tissue 40 with suture (not shown). This may be performed before or after the suture sleeve 16 is secured to the lead 30 since the suture wing 14 is offset from the flexible strap 16.

Once the suture sleeve 10 is secured to the lead 30 as described above, the excess flexible strap may be cut off. This may be readily done since the flexible strap excess is conveniently exposed.

Figure 4:
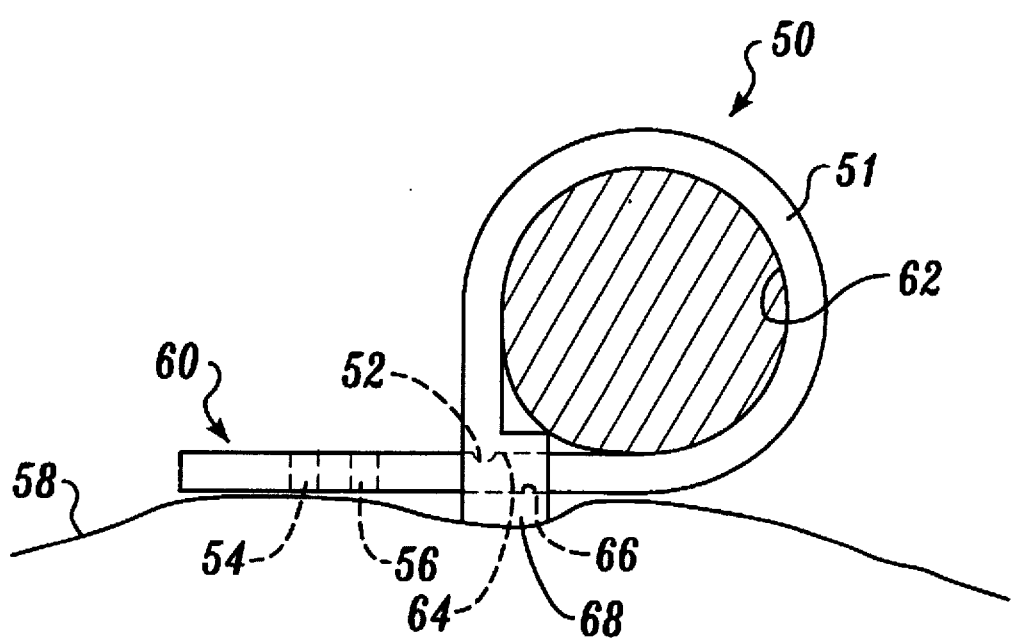
FIG. 4 is a side plan view illustrating an other suture sleeve embodying the present invention in use.

Referring now to FIG. 4, it illustrates another suture sleeve 50 embodying the present invention. The suture sleeve 50 is similar to the suture sleeve 10 except that it has only one ratchet tooth 52 on the flexible strap 51 and the suture holes 54 and 56 for securing the suture sleeve to body tissue 58 with suture (not shown) are located in the flexible strap 51 at a distal end 60 thereof. Hence, the single ratchet tooth 52 defines the confirming perimeter 62 when engaging the pawl 64 within the channel 66 of base 68. As can be readily seen in FIG. 4, the operations of the suture sleeve 50 is essentially the same as that of suture sleeve 10 of FIGS. 1–3.

While a particular embodiment of the present invention has been shown and described, modifications may be made, and it is therefore intended in the appended claims to cover all such changes and modifications which fall within the true spirit and scope of the invention.

What is claimed is:

1. A suture sleeve for gripping the body of an implanted lead associated with an implanted cardiac device for fixation of the lead with respect to body tissue the suture sleeve comprising:

a base;

securing means for securing the suture sleeve to body tissue;

a flexible strap extending from the base;

receiving means carried by the base for receiving the flexible strap and permitting the strap to pass therethrough;

the strap defining a confining perimeter when encircling the lead body and received by the receiving means;

locking means for locking the flexible strap with respect to the receiving means; and limit means for limiting a locked confining perimeter defined by the flexible strap to a predetermined minimum dimension.

2. A suture sleeve as defined in claim 1 wherein the flexible strap includes a plurality of ratchet teeth carried by the flexible strap and wherein the locking means comprises a pawl for lockingly engaging the ratchet teeth.

3. A suture sleeve as defined in claim 2 wherein the pawl is formed in the receiving means.

4. A suture sleeve as defined in claim 2 wherein the plurality of ratchet teeth include a ratchet tooth most proximal to the base and wherein the limit means include the most proximal ratchet tooth.

5. A suture sleeve as defined in claim 4 wherein the lead body has a circumference and wherein the spacing between the most proximal ratchet tooth and the base is slightly less than the lead body circumference.

6. A suture sleeve as defined in claim 1 wherein the securing means are formed in the base.

7. A suture sleeve as defined in claim 1 wherein the securing means include at least one suture hole.

8. A suture sleeve as defined in claim 1 wherein the securing means is formed in the flexible strap.

9. A suture sleeve as defined in claim 8 wherein the securing means comprise at least one suture hole.

10. A suture sleeve as defined in claim 8 wherein the flexible strap has a distal end and wherein the securing means are formed in the distal end of the flexible strap.

11. A suture sleeve as defined in claim 1 wherein the locking means comprises a pawl and wherein the limit means comprises a ratchet tooth within the flexible strap for lockingly engaging the pawl.

* * * * *